United States Patent [19]

Bartko et al.

[11] 4,043,755
[45] Aug. 23, 1977

[54] METHOD AND APPARATUS FOR DETERMINING URANIUM CONCENTRATION IN A MOVING STREAM

[75] Inventors: John Bartko, Monroeville; James W. Wonn, Hemfield Township, both of Pa.

[73] Assignee: Westinghouse Electric Corporation, Pittsburgh, Pa.

[21] Appl. No.: 671,886

[22] Filed: Mar. 29, 1976

[51] Int. Cl.$^2$ .................................................. G01N 31/00
[52] U.S. Cl. .............................. 23/230 R; 23/230 EP; 176/19 R; 324/71 CP
[58] Field of Search ....................... 250/336, 390–392; 176/19 R, 19 LD; 73/19, 61 R; 324/71 CP; 235/92 PC; 23/230 R, 230 EP

[56] References Cited

PUBLICATIONS

Journal of the Acoustical Society of America, vol. 45, pp. 515–518, Marietti et al., (1969).

ASTM-Standard, E 318-69, (Mar. 21, 1969).

Primary Examiner—Samuel W. Engle
Assistant Examiner—S. A. Cangialosi
Attorney, Agent, or Firm—R. D. Fuerle

[57] ABSTRACT

The concentration of uranium in a moving stream is determined by agglomerating background microbubbles out of the 6 to 10 micron size range, counting microbubbles in the stream which are about 6 to about 10 microns in size, exposing the stream to a radiation source to cause uranium fission fragments to produce microbubbles, countng microbubbles which are about 6 to about 10 microns in size, and subtracting one count from the other and multiplying by a calibration constant. The subtraction can be performed on an earlier first count so that both counts are made on the same volume. The radiation exposure can be automatically increased when the difference between the first and second counts is low.

27 Claims, 1 Drawing Figure

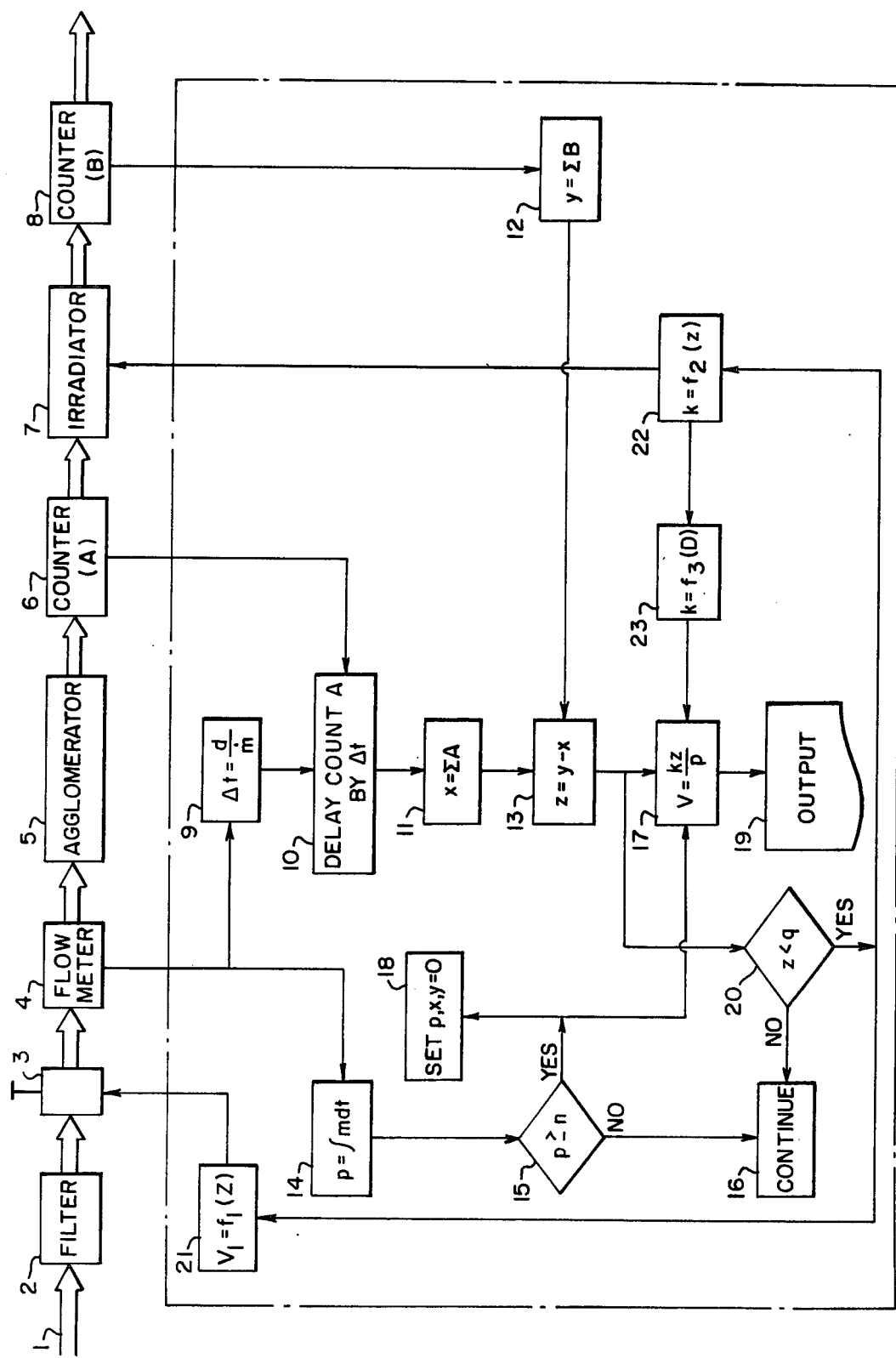

METHOD AND APPARATUS FOR DETERMINING URANIUM CONCENTRATION IN A MOVING STREAM

BACKGROUND OF THE INVENTION

In solution mining a specially prepared solution is placed in boreholes in areas known to contain low concentrations of uranium, typically about 10 to 100 ppm. The solution leaches the uranium out of the rock structure and is then pumped to the surface.

When the solution reaches the surface it must be determined whether it contains enough uranium to justify the costs of extracting the uranium from the solution. Since large quantities of fluids are involved, and storage facilities are usually not available this determination must be made immediately. The information, of course, is also needed to determine the profitability of particular boreholes and to compensate the land owner for the uranium, but here the urgency is not present.

Conventional chemical analysis can be used, but it is time consuming and requires skilled personnel. Also, the concentration of uranium may change rapidly resulting in uneconomical extraction or the loss of uranium.

PRIOR ART

An article entitled "Detection of Cavities Produced in a Liquid by Ionizing Particles," by P. Marcetti, D. Sette, and F. Wanderlingh in The Journal of the Acoustical Society of America, Volume 45, January –June 1969, discloses counting microbubbles in a static solution, adding uranium, irradiating with neutrons, irradiating with sound, re-counting, subtracting one count from the other, and relating the difference to bubble concentration.

The agglomeration of microbubbles using ultrasonic sound is a known technique.

The irradiation of uranium fission fragments is known to produce microbubbles in the 6 to 10 micron range.

SUMMARY OF THE INVENTION

We have invented an apparatus and a process for determining uranium concentration in a moving aqueous stream. In our process microbubbles in the 6 to 10 micron range are increased in size, then microbubbles in that range are counted, the stream is irradiated, the microbubbles recounted, and the difference is multiplied by a calibration constant to give uranium concentration.

This method provides a continuous and immediate determination of uranium content in a moving stream. The apparatus is fully automated and does not require a skilled operator. Because bubbles from fission fragments are counted, which are at least twice as numerous as bubbles from alpha particles, the method of this invention is very sensitive to variations in uranium concentration.

DESCRIPTION OF THE INVENTION

The accompanying drawing is a schematic view of a certain presently preferred embodiment according to this invention for determining uranium concentration in a moving stream. The blocks within the dotted lines are calculations which are performed, and the area above the top dotted line is apparatus.

In the drawings a stream 1, which may be the total stream or only a portion thereof, passes through filter 2 which removes the larger particles suspended therein. The stream moves through flow control valve 3 and flow meter 4 to agglomerator 5.

It is the purpose of the agglomerator to increase the size of bubbles in the stream which are in the range of about 6 to about 10 microns. These bubbles are formed by turbulence in the stream and are agglomerated so that they do not interfere with the determination of the concentration of uranium. The agglomeration may be advantageously accomplished ultrasonically, as is known to the art. Ultrasonic agglomeration will merge all microbubbles into a lesser number of large ($>>$ 10 micron), stable bubbles.

The stream then passes to counter 6 which produces a pulse A for each microbubble detected in the 6 to 10 micron range. While it is desired to count only bubbles, most counters will also count any type of particle in that range. A preferred counter is the Coulter counter which forces the stream through a small aperture and measures current flow from one side of the aperture to the other, the decrease in current being proportional to the size of the particle. An ultrasonic counter may also be used but it is not preferred because it is not as precise.

Irradiator 7 then irradiates the stream with neutrons or gamma rays, in order to cause the uranium fission fragments to produce microbubbles. Neutrons are preferred because neutron sources are small and easily obtained while gamma ray sources require large machines. Examples of standard neutron sources include Am-Be, Ra-Be, Cm-Be, Pu-Be, $252_{Cf}$, or a neutron-producing machine. The preferred neutron sources are Am-Be and $252_{Cf}$ because they are inexpensive. These sources produce fast neutrons which must be slowed to thermal neutrons in order to produce microbubbles when they strike uranium fission fragments. They are slowed by the water itself, but preferably the stream flows through a plastic pipe because the hydrogen in the plastic increases the thermal neutron flux. Polyethylene, polypropylene, or other plastics may be used. Also, a metal pipe surrounded by paraffin can be used, but metal is not as effective because it absorbs neutrons. A preferred fast neutron source strength is about $10^7$ to about $10^9$ fast neutrons per second. A preferred thermal neutron flux in the stream is about $10^4$ to about $10^6$ thermal neutrons per centimeter per second.

After irradiation, the stream passes to a second counter 8, similar to counter 6, which produces pulses B for each microbubbles detected in the range of about 6 to about 10 microns.

The determination of uranium concentration is made in the following manner. Flow meter 4 determines the flow rate of the stream $\dot{m}$. The flow rate, $\dot{m}$, is used, in block 9, to calculate $\Delta t$ which is equal to $d$, the (constant) volume of the liquid in the apparatus between counter 6 and counter 8, divided by $\dot{m}$, flow rate. Thus, $\Delta t$ is the time required for an incremental volume element to pass from counter 6 to counter 8. In block 10 the pulses A from counter 6 are delayed by time $\Delta t$, so that the comparison between counts will be made on the same volume of the stream. In block 11 pulses A are summed to give X, the total count from counter 6. Similarly, in block 12 pulses B are summed to give Y, the total count from counter 8. In block 13 $x$ is substracted from $y$ to give $z$, the additional number of bubbles produced by the irradiation, which is proportional to the uranium concentration.

In block 14 the flow rate $\dot{m}$ is integrated over time to give p, the volume of fluid which has passed through the flow meter. In test block 15 it is determined whether the volume equals or exceeds a predetermined volume, $n$, over which the determination of uranium concentration is to be made. If not, the process continues (block 16), but if $p$ does equal or exceed $n$, then the calculation of uranium concentration is made (block 17) by multiplying $z$ by a proportionality constant, $k$ and dividing by the volume, $p$, and $p$, $x$, and $y$ are set to zero (block 18). The U in block 17 is the output 19 in units of concentration per unit volume.

If the difference, $z$, in total count from counters 6 and 8 in block 20, is determined to be larger than a predetermined number $q$, the process continues (block 16). But if the difference $z$ is smaller than $q$ due, for example, to the presence of a large number of unfilterable background particles, it is desirable to increase the sensitivity and precision of the determination. This may be accomplished by altering the exposure of the stream to irradiation in two ways, both shown on the drawing though only one need be used. In the first method the flow rate is decreased so that the stream is exposed to irradiation for a longer period of time. This method is preferred because accuracy at low uranium concentrations can be increased by using maximum irradiation exposure at low flow rates. In block 21 valve 3 is opened or closed according to $V_1$, which is a function of $z$. In the alternative method, in block 22, $V_2$, also a function of $z$, is calculated and is used to control the exposure of the stream to the irradiation source. This may be accomplished by altering the distance between the stream and the source or by shielding the stream from the source, for example, with cadmium or gadolinium shields. Altering the distance is preferred as it is simpler. If this alternative method is used it is necessary to re-compute, in block 23, the proportionality constant, K, as a function of D, the exposure of the stream to the source of irradiation. The apparatus is initially calibrated to determine K preferably by passing several solutions of known uranium concentration therethrough.

Although the above-described apparatus is preferred, several variations are considered to be within the scope of this invention. For example, after agglomerator 4 the stream may be divided into two portions, one having counter 6 and the other having irradiator 7 and counter 8, thus eliminating the need for delaying the signal from counter 6.

We claim:
1. A method of determining the concentration of uranium in a moving liquid stream comprising:
   1. increasing the size of microbubbles in said stream which are about 6 to about 10 microns until they are larger than about 10 microns;
   2. counting microbubbles in a given volume of said stream which are about 6 to about 10 microns in size;
   3. exposing said stream to a source of radiation which causes uranium fission fragments to produce microbubbles;
   4. counting microbubbles in said given volume of said stream which are about 6 to about 10 microns in size; and
   5. subtracting the number of microbubbles counted in step (2) from the number counted in step (4) and multiplying the difference by a calibration constant.
2. A method according to claim 1 wherein said stream is filtered prior to step (1).

3. A method according to claim 1 wherein the exposure of said stream to said source of radiation is a function of said difference.
4. A method according to claim 1 wherein the exposure of said stream to said radiation is controlled by the flow rate of said stream past said source of radiation.
5. A method according to claim 1 wherein the flow rate of said stream past said counters is measured and said counts are made over a predetermined volume of said stream.
6. A method according to claim 1 including the initial step of determining said calibration constant by applying said method to a liquid containing a known concentration of uranium, and dividing said concentration by said difference.
7. A method according to claim 1 wherein the size of microbubbles is increased by agglomeration with ultrasonic sound.
8. A method according to claim 1 wherein said subtraction is performed on a count made by step (2) at about $\Delta t$ seconds before the count was made in step (4), where $\Delta t = d/\dot{m}$ where $d$ is the fluid volume between the step (2) count and the step (4) count and $\dot{m}$ is the flow rate of the stream.
9. A method according to claim 1 wherein said source is a neutron source.
10. A method according to claim 9 wherein said source is Am-Be or Cf.
11. A method according to claim 9 wherein said neutrons are fast neutrons and said liquid is enclosed in a material rich in hydrogen.
12. A method according to claim 9 wherein the strength of said neutron source is about $10^7$ to about $10^9$ fast neutrons/sec.
13. A method according to claim 9 wherein the flux of said neutrons in said stream is about $10^4$ to about $10^6$ thermal neutrons/cm²/sec.
14. Apparatus for determining uranium concentration in a moving liquid stream comprising:
   A. an agglomerator for increasing the size of microbubbles in said stream which are about 6 to about 10 microns until they are larger than about 10 microns;
   B. a first counter for counting microbubbles in a given volume of said stream which are about 6 to about 10 microns in size;
   C. an irradiator for exposing said stream to a source of radiation which causes uranium fission fragments to produce microbubbles;
   D. a second counter for counting microbubbles in said given volume of said stream which are about 6 to about 10 microns in size; and
   E. calculating means for subtracting the number of microbubbles counted by said second counter from the number counted by said first counter and for multiplying the difference by a calibration constant.
15. Apparatus according to claim 14 including a filter upstream of said agglomerator for filtering said moving liquid stream.
16. Apparatus according to claim 14 including means for controlling the exposure of said stream to said source of radiation so that said exposure is a function of said difference.
17. Apparatus according to claim 14 including means for controlling the exposure of said stream to said source of radiation by changing the flow rate of said stream past said source of radiation.
18. Apparatus according to claim 14 including a flow meter for measuring the flow rate of said stream past said counters, said calculating means determining said difference over a predetermined volume of said stream as calculated from said flow rate.

19. Apparatus according to claim 14 wherein said agglomerator increases the size of said microbubbles by means of ultrasonic sound.

20. Apparatus according to claim 14 including means for storing the count made by said first counter for $\Delta t$ seconds, where $\Delta t = d/\dot{m}$, where $d$ is the fluid volume between said first counter and said second counter and $\dot{m}$ is the flow rate of said stream, so that said calculating means performs said subtraction on counts made on the same volume of said stream.

21. An apparatus according to claim 14 wherein said source of radiation is a neutron source.

22. An apparatus according to claim 21 wherein said neutron source is Am-Be or Cf.

23. An apparatus according to claim 21 wherein said neutrons are fast neutrons and said liquid is enclosed in a material rich in hydrogen.

24. An apparatus according to claim 21 wherein the strength of said neutron source is about $10^7$ to about $10^9$ fast neutrons/sec.

25. An apparatus according to claim 21 wherein the flux of said neutrons in said stream is about $10^4$ to about $10^6$ thermal neutrons/cm$^2$/sec.

26. Apparatus according to claim 14 wherein said first and second counters count microbubbles by forcing said stream through a small aperture and measuring current flow from one side of said aperture to the other.

27. A method according to claim 1 wherein said microbubbles are counted by forcing said stream through a small aperture and measuring current flow from one side of said aperture to the other.

* * * * *